United States Patent [19]

Mura et al.

[11] Patent Number: 5,110,723

[45] Date of Patent: May 5, 1992

[54] METHOD FOR PROVIDING CHEMICALLY OR BIOLOGICALLY USEFUL MOIETY FROM WATER-COMPATIBLE REDUCIBLE COMPOUND

[75] Inventors: Albert J. Mura, Rochester; Robert T. Belly, Webster; Vanessa R. Lum, Rochester, all of N.Y.

[73] Assignee: Eastman Kodak Company, Rochester, N.Y.

[21] Appl. No.: 660,369

[22] Filed: Feb. 25, 1991

Related U.S. Application Data

[62] Division of Ser. No. 344,869, Apr. 28, 1989, Pat. No. 5,037,762, which is a division of Ser. No. 868,855, May 30, 1986, Pat. No. 4,853,186.

[51] Int. Cl.$^5$ ............................................. C12Q 1/00
[52] U.S. Cl. .......................................... 435/4; 436/174; 436/166; 436/164; 436/904; 436/169; 422/56; 435/7.32; 435/7.21; 435/7.31; 435/805
[58] Field of Search ..................... 435/25, 29, 34, 805, 435/28, 47.21, 7.31, 7.32; 436/169, 174, 93, 94, 63, 120, 170, 518, 904, 166, 164; 422/56, 57, 60

[56] References Cited

U.S. PATENT DOCUMENTS

| | | |
|---|---|---|
| 3,980,479 | 9/1976 | Fields et al. . |
| 4,108,850 | 8/1978 | Fields et al. . |
| 4,139,379 | 2/1979 | Chasman et al. . |
| 4,144,306 | 3/1979 | Figueras . |
| 4,232,107 | 11/1980 | Janssens . |
| 4,307,188 | 12/1981 | White . |
| 4,371,604 | 2/1933 | Van de Sande et al. . |
| 4,746,607 | 5/1988 | Mura et al. ............................ 435/25 |
| 4,857,271 | 8/1989 | Belly et al. ............................ 422/55 |

OTHER PUBLICATIONS

Van de Sande, Angew. Chem. Int. Ed. Engl., 22 pp. 191-209 (1983).

Primary Examiner—Robert J. Hill, Jr.
Assistant Examiner—Thomas E. Daley
Attorney, Agent, or Firm—J. Lanny Tucker

[57] ABSTRACT

Certain water-compatible reducible compounds are useful in analytical compositions and elements for assay of various analytes, e.g. microorganisms. These compounds comprise a moiety which provides a detectable species (e.g. a dye) when released from the compound at physiological pH. Further, these compounds are aromatic derivatives or quinones having water-compatibilizing substituents which allow them to be used in compositions without the use of surfactants.

10 Claims, No Drawings

METHOD FOR PROVIDING CHEMICALLY OR BIOLOGICALLY USEFUL MOIETY FROM WATER-COMPATIBLE REDUCIBLE COMPOUND

This is a divisional of application Ser. No. 344,869, filed Apr. 28, 1989, now U.S. Pat. No. 5,037,762, which is a divisional of application Ser. No. 868,855, filed May 30, 1986, now U.S. Pat. No. 4,853,186.

FIELD OF THE INVENTION

This invention relates to clinical chemistry. In particular, it relates to water-compatible reducible compounds which can be reduced to provide a detectable species, and to analytical compositions and elements containing same. It also relates to a method for the determination of analytes in, e.g. biological fluids.

BACKGROUND OF THE INVENTION

Chemical analysis of liquids, such as water, milk and biological fluids is often desirable or necessary for health maintenance and diagnostic care. Various compositions and elements to facilitate such analyses are known. Such compositions and elements generally include a reagent composition for determining a substance under analysis, identified as an "analyte" herein. The analyte can be a living organism or a nonliving chemical substance. The reagent composition, upon interaction with the analyte, provides a detectable change (e.g. dye formation).

Recently, much work has been directed to developing compositions and elements which are useful for rapid and highly quantitative diagnostic or clinical analysis of biological fluids such as whole blood, serum, plasma, urine and the like.

For example, for the rapid and effective diagnosis and treatment of infectious diseases, it is desirable to be able to detect the bacteria causing the disease as rapidly as possible. Infections of the urinary tract are among the most common bacterial diseases, second in frequency only to infections of the respiratory tract. In fact, in many hospitals, urinary tract infections are the most common form of nosocomial infections, often following the use of in-dwelling catheters and various surgical procedures. Most urinary tract infections (UTI) result from ascending infection by microorganisms introduced through the urethra and vary in severity from an unsuspected infection to a condition of severe systemic disease. Such infections are usually associated with bacterial counts of 100,000 ($10^5$) or more organisms per ml of urine, a condition referred to as significant bacteriuria. Under normal conditions, urine is sterile, although contamination from the external genitalia may contribute up to 1,000 ($10^3$) organisms per ml in properly collected and transported specimens.

A significant advance in the detection of microorganisms and other analytes capable of reducing a reducible compound is described and claimed in copending and commonly assigned U.S. Ser. No. 824,766, filed Jan. 31, 1986 by Belly et al and entitled REDUCIBLE COMPOUNDS AND ANALYTICAL COMPOSITIONS, ELEMENTS AND METHODS UTILIZING SAME, now U.S. Pat. No. 4,857,271. The assay described in that application utilizes reducible compounds which release a detectable species in the presence of the analyte. While providing a highly advantageous assay, the reducible compounds described therein generally have limited solubility in aqueous solutions. Hence, water-solubilizing surfactants must be used in the practice of the Belly et al invention to prepare compositions of the reducible compounds.

The use of surfactants in such compositions has serious drawbacks. Surfactants tend to lyse certain cells (e.g. white blood cells) thereby making it difficult to detect or identify such cells. Hence, there is a need in the art for a rapid and highly sensitive assay using reducible compounds which avoids the use of surfactants.

SUMMARY OF THE INVENTION

The present invention overcomes the problems of the art with the use of certain water-compatible reducible compounds of the structure CAR—(R$^1$)$_n$ wherein CAR— is a substituted or unsubstituted aromatic or quinone nucleus, R$^1$ is a moiety which comprises a shiftable detectable species, and n is 1 or 2, provided the reducible compound is capable of being reduced at a pH of 9 or less to release the shiftable detectable species and comprises at least one water-compatibilizing moiety, and further provided that when R$^1$ is replaced with H, CAR—(H)$_n$ has an E$_{\frac{1}{2}}$ of at least about +100 mV when measured in water.

Particularly useful water-compatible reducible compounds are of the structure CAR—R$^1$ wherein CAR— is

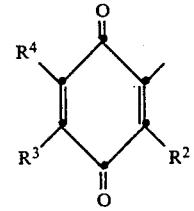

R$^1$ is

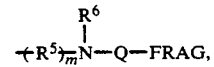

R$^2$ and R$^4$ are independently hydrogen, substituted or unsubstituted alkyl, substituted or unsubstituted aryl or an electron withdrawing group, R$^3$ is R$^1$, hydrogen, substituted or unsubstituted alkyl, substituted or unsubstituted aryl or an electron withdrawing group, provided that at least one of R$^2$, R$^3$ and R$^4$ is an electron withdrawing group, or R$^3$ and R$^4$, taken together, represent the atoms necessary to complete a substituted or unsubstituted strained fused carbocyclic ring, R$^5$ is substituted or unsubstituted alkylene of 1 or 2 carbon atoms, R$^6$ is substituted or unsubstituted alkyl, substituted or unsubstituted cycloalkyl or substituted or unsubstituted aryl, Q is carbonyl or thiocarbonyl, FRAG is a shiftable detectable species which provides a detectable species when released from the reducible compound, and m is 0 or 1, provided that when R$^1$ is replaced with H, CAR—H has an E$_{\frac{1}{2}}$ of at least about +100 mV when measured in water, and further provided that at least one of $R^1$, $R^2$, $R^3$ or $R^4$ comprises at least one water-compatibilizing moiety.

The present invention also provides an aqueous composition buffered at a pH of 9 or less which consists essentially of the water-compatible reducible compound described above.

Also, a dry analytical element for the determination of an analyte comprises an absorbent carrier material and contains the water-compatible reducible compound described above.

This invention also provides a method for the determination of an analyte comprising the steps of:
  A. contacting a sample of a liquid suspected of containing an analyte with the water-compatible reducible compound described above, and
  B. detecting the detectable species released as a result of the presence of the analyte.

The present invention provides a means for using reducible compounds in rapid and highly quantitative determinations of analytes, e.g. enzymes, metabolites or living cells (e.g. bacteria, yeast, fungi, white blood cells, etc.) in liquids at physiological pH (i.e. 9 or less). These reducible compounds can be dissolved in coating compositions or solution assay compositions without the use of surfactants. Therefore, the problem encountered with the use of surfactants (i.e. adverse affect on cells) is avoided. In addition, it was unexpectedly found that the sensitivity of the assay was improved in the absence of surfactants. This invention also provides a means for releasing chemically or biologically useful moieties which can be converted into detectable species. These advantages have been achieved by incorporating water-compatibilizing groups in reducible compounds.

DETAILED DESCRIPTION OF THE INVENTION

The water-compatible reducible compounds useful in the practice of this invention are broadly defined as water-compatible organic compounds containing a shiftable detectable species which can be reduced at physiological pH (i.e. 9 or less) to release the shiftable detectable species. The term "shiftable" is defined as: (1) a chromogen moiety, which has a first spectral absorption band while attached to the reducible compound and a second spectral absorption band when released, or a fluorogen moiety, which has first spectral excitation and emission bands while attached to the reducible compound and second spectral excitation and emission bands when released, (2) a chemically or biologically useful moiety which is inactive, blocked or otherwise inaccessible when attached to the reducible compound but active, unblocked or accessible when released, or (3) a chemically or biologically useful moiety which is active or accessible when attached to the reducible compound but inactive or otherwise inaccessible when released.

Thus, the detectable species is chemically modified when attached to the reducible compound, e.g. for (1) above the spectral band or bands of the reducible compound are "shifted" from the band or bands that the species has when released. Generally, but not necessarily, the band or bands are relocated to substantially shorter wavelengths when the species is a part of the reducible compound. In all cases, the bands do not overlap to a significant extent. The change (i.e. "shift") from one spectral band to another can be due to the mere release of the moiety from the reducible compound, or alternatively, it can be caused by such release coupled with either interaction of the released moiety with metal ions or a mordant, or coupled with a change in the assay environment e.g. change in pH). With any such change in the environment, the pH must remain at 9 or less.

Also, as noted above, the shiftable detectable species can also be a chemically or biologically useful moiety which, when attached to the water-compatible reducible compound, is inactive or blocked or otherwise inaccessible, but when released at physiological pH becomes biologically or chemically active or accessible for further interaction. The released, active species can be detectable itself or is capable of one or more subsequent chemical, physical or biological reactions to provide a detectable species. The method of this invention provides a means for releasing such moieties, e.g. electron transfer agents, enzymes, enzyme substrates, enzymes inhibitors, cofactors, catalysts, reactants, etc. upon reduction of the reducible compound, preferably at physiological pH, for a variety of chemical or biological purposes.

Further, a shiftable detectable species can be a chemically or biologically useful moiety which, when attached to the reducible compound, is active, or otherwise accessible for one or more subsequent chemical, physical or biological reactions, but when released at physiological pH becomes inactive or otherwise inaccessible for such reactions.

The reducible compounds described herein are water-compatible, which is defined as being more readily dissolvable (or soluble) in polar organic solvents (e.g. alcohols, acetonitrile, N,N-dimethylformamide, dimethylsulfoxide, etc.), water or aqueous solutions containing a minor amount of one or more polar organic solvents, than in nonpolar organic solvents. Which solvents are polar and nonpolar is readily determinable by one of ordinary skill in the art. This water-compatibility is imparted by one or more water-compatibilizing substituents on the compound. Such substituents are broadly defined as moieties which have a hydrophobic parameter ($P_i$) less than about $-2.0$. Such a parameter is a standard value for a given moiety as described, for example, in *Quantitative Drug Design* by Y. Martin, Marcel Dekker, Inc., New York, 1978. These moieties are either readily ionizable in water (e.g. carboxy or sulfo) or nonionizable in water (e.g. iodoxy or glucosyl). A preferred water-compatibilizing substituent is carboxy. Other useful substituents include hydroxy, quaternary ammonium, sulfonamido, etc. The substituents can be placed on the CAR— portion of the molecule or on the $R^1$ portion, or on both. Examples of such compounds and the placement of the water-compatibilizing substituents are provided below in Table I without intending to limit the scope of this invention.

More particularly, the compounds useful in this invention have the structure CAR$-(R^1)_n$ wherein CAR— represents a substituted or unsubstituted aromatic or quinone nucleus, $R^1$ is a moiety comprising a shiftable detectable species defined below, and n is 1 or 2. Examples of such nuclei are presented below. Further, when $R^1$ is replaced by H, CAR$-(H)_n$ has a reduction potential ($E_{\frac{1}{2}}$) of at least about $+100$ mV when measured in water. This $E_{\frac{1}{2}}$ value facilitates the reduction and subsequent release of the shiftable detectable species from the compound at physiological pH (i.e. 9 or less). Such measurements are made according to standard electrochemical techniques using either differential pulse polarography or cyclic voltametry (see, e.g. Sawyer and Roberts, Jr., *Experimental Electrochemistry for Chemists*, John Wiley & Sons, New York, 1974). Preferably, the $E_{\frac{1}{2}}$ is from about $+100$ mV to about $+400$ mV as measured in water. Further details of measuring the $E_{\frac{1}{2}}$ are described below prior to Table I. The desired $E_{\frac{1}{2}}$ is achieved by appropriate electron withdrawing groups on the CAR— nucleus, or by a strained fused ring attached to the nucleus or by a combination of both.

In one embodiment, the water-compatible reducible compounds can be reduced to provide a detectable species through quinonemethide formation, similar to the description by Van de Sande in *Angew. Chem. Int. Ed. Engl.* 22, pp. 191–209 (1983) and U.S. Pat. No. 4,232,107 (issued Nov. 4, 1980 to Janssens), but which have the desired $E_{178}$ properties and one or more water-compatibilizing groups.

In another embodiment, useful water-compatible reducible compounds include sulfilimides and sulfenylsulfonamides similar to those described on page 206 of the Van de Sande reference noted above, but which have the desired $E_{\frac{1}{2}}$ properties and one or more water-compatibilizing groups.

In a preferred embodiment, the water-compatible reducible compounds of this invention are RIND compounds, i.e. reducible compounds capable of undergoing intramolecular nucleophilic displacement at physiological pH to release one or more shiftable detectable species when a nucleophilic group is generated by at least a one electron reduction of the compound. In other words, such displacement occurs when the RIND compound is reduced by a suitable reductant which provides one or more electrons (described in more detail below). The distinction of these RIND compounds over the many similar benzoquinone compounds used in the photographic art is that the RIND compounds have a higher $E_{\frac{1}{2}}$ value, thereby facilitating their reduction and subsequent release of a shiftable detectable species (e.g. a dye) at physiological pH (i.e. 9 or less).

The term "intramolecular nucleophilic displacement" refers to a reaction in which a nucleophilic center on a molecule reacts at another site in the molecule, which site is an electrophilic center, to effect displacement of a group or atom attached to the electrophilic center. Generally, the RIND compounds useful in this invention have the nucleophilic and electrophilic groups juxtaposed in the three-dimensional configuration of the molecule in close proximity whereby the intramolecular reaction can take place and a ring is formed having from 4 to 7 atoms, and preferably having 5 or 6 atoms.

Particularly useful water-compatible RIND compounds are those which have the structure CAR—$R^1$ wherein CAR— is

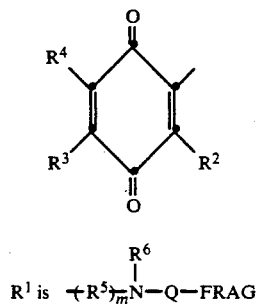

$R^1$ is $+R^5)_{\overline{m}}N-Q-FRAG$ wherein m is 0 or 1, and preferably 1. $R^5$ is substituted or unsubstituted alkylene, preferably of 1 or 2 carbon atoms in the backbone (e.g. methylene, ethylene, alkoxymethylene, etc.). Most preferably, $R^5$ is methylene. Q is carbonyl or thiocarbonyl and preferably carbonyl.

$R^6$ is substituted or unsubstituted alkyl preferably of 1 to 10 carbon atoms (e.g. methyl, ethyl, n-propyl, isopropyl, t-butyl, hexyl, decyl, benzyl, etc.), substituted or unsubstituted cycloalkyl preferably of 4 to 12 carbon atoms (e.g. cyclobutyl, cyclohexyl, 4-methylcyclohexyl, etc.), or substituted or unsubstituted aryl of 6 to 12 carbon atoms (e.g. phenyl, xylyl, naphthyl, p-nitrophenyl, p-t-butoxyphenyl, etc.). Preferably, $R^6$ is lower alkyl of 1 to 3 carbon atoms (substituted or unsubstituted), and more preferably, it is methyl.

FRAG is a shiftable detectable species as defined above. Preferably, along with the remainder of the molecule, it has a first spectral band, but when it is cleaved from the RIND compound, it provides a detectable species having a second spectral band. This species is released in an amount which can be directly related to the amount of reductant present. The specific composition of FRAG can vary considerably depending upon the type of detectable species desired and upon the particular detection means employed.

The shiftable detectable species can be a material which is directly detectable by a suitable means, as well as a material which can react with other substances, e.g. analytes, enzymes or other reagents to provide a detectable species. Such species include those detectable by radiometric means, including chromogens (e.g. dyes or pigments) which can be detected colorimetrically and fluorogens (e.g. fluoroscent dyes or probes) which can be detected fluorometrically. Additionally, the detectable species can be a phosphorescent species, a chemiluminescent species, or any other detectable species known to one skilled in the art.

Particularly useful shiftable detectable moieties are chromogens and fluorogens having a first spectral band(s) prior to release and a second spectral band(s) when measured after release. Examples of useful classes of chromogens are azo, azomethine, nitrophenol, indophenol, indoaniline and triarylmethane dyes, and others known in the art, with azo dyes being preferred. Examples of useful classes of fluorogens are coumarins, 4-oxo-4H-benz-[d,e]anthracene and its derivatives, phenalenones and benzphenalenones, fluorescein and rhodamine fluorescent dyes, and others known in the art. Phenalenone dyes are particularly useful.

Useful phosphorescent species include such phosphors as 2',5'-dibromofluorescein and 4',5'-diiodofluorescein. A useful chemiluminescent species is luciferin.

FRAG is linked to Q by means of a single bond through a bivalent monoatom linkage which is a part of FRAG. Preferably, the monoatom linkage is oxy, thio or seleno when FRAG is a chromogen and oxy or thio when FRAG is a fluorogen. Most preferably, Q is oxy.

$R^2$, $R^3$ and $R^4$ in the above quinone structure are independently hydrogen, substituted or unsubstituted alkyl of 1 to 10 carbon atoms (e.g. methyl, ethyl, hydroxymethyl, methoxymethyl, benzyl, etc.) substituted or unsubstituted aryl (e.g. phenyl, naphthyl, methylnaphthyl, p-nitrophenyl, m-methoxyphenyl, phenylsulfonamido, etc.) or an electron withdrawing group which generally has a positive Hammett sigma value, and preferably has a sigma value greater than about 0.06. Hammett sigma values are calculated in accordance with standard procedures described, e.g. in *Steric*

*Effects in Organic Chemistry*, John Wiley & Sons, Inc., 1956, pp. 570–574 and *Progress in Physical Organic Chemistry*, Vol. 2, Interscience Publishers, 1964, pp. 333–339. Representative electron withdrawing groups having positive Hammett sigma values include cyano, carboxy, nitro, halo (e.g. fluoro, bromo, chloro, iodo), trihalomethyl (e.g. trifluoromethyl, trichloromethyl, etc.), trialkylammonium, carbonyl, carbamoyl, sulfonyl, sulfamoyl, esters and others known in the art, or alkyl or aryl groups (defined above) substituted with one or more of these electron withdrawing groups. Preferred electron withdrawing groups include p-nitrophenyl, m-nitrophenyl, p-cyanophenyl and 2,5-dichlorophenyl. Aryl groups with methoxy or acetamido groups in the meta position are also useful.

Homologues of $R^2$, $R^3$, $R^4$ or $R^6$ having more carbon atoms than those described above may also be useful in this invention, but it must be understood that such increased hydrophobicity may require additional water-compatibilizing substituents over the smaller homologues.

$R^3$ can also be $R^1$ thereby potentially providing a 2:1 molar ratio of detectable species molecules to original RIND compound molecules.

Alternatively, $R^3$ and $R^4$, taken together, can represent the carbon atoms necessary to complete a substituted or unsubstituted strained fused carbocyclic ring attached to the quinone nucleus. Ring strain makes reduction potentials more positive, e.g. see Rieke et al, *Tetrahedran Letters*, No. 50, pp. 4381–4384 (1969). For example, such a ring (mono- or bicyclic) can have from 4 to 8 carbon atoms in the backbone, and is preferably a 5-membered mono- ring or a 7- or 8-membered bicyclic ring.

In the RIND compounds described above, the water-compatibilizing moiety is a part of one or more of $R^1$, $R^2$, $R^3$ or $R^4$. Preferably, it is a part of $R^2$, or of $R^6$ or FRAG which are parts of $R^1$ defined above.

Representative and preferred RIND compounds of this invention are listed in Table I below in reference to the following structure:

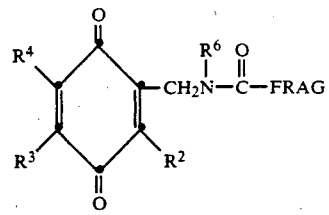

The $E_{\frac{1}{2}}$ values in Table I were determined for the quinone nucleus of this structure having a hydrogen atom in place of

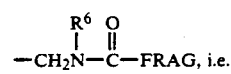

i.e.

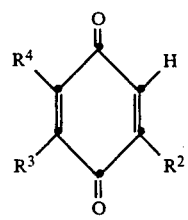

The $E_{\frac{1}{2}}$ values (where available) were measured in an aqueous solution of the quinone including N,N-dimethylformamide and sodium phosphate buffer (pH 7). A standard calomel electrode was used as a standard. The $E_{\frac{1}{2}}$ values were corrected to a normal hydrogen electrode (NHE). $E_{\frac{1}{2}}$ values not available are denoted by "NA".

TABLE I

| RIND Compound | $R^6$ | $R^2$ | $R^4$ | $R^3$ | FRAG | $E_{\frac{1}{2}}$ (mV,NHE) |
|---|---|---|---|---|---|---|
| I. | —CH₃ | —⟨ ⟩—CN | $R^3$ and $R^4$ together form ⟨ ⟩ | | —O—⟨ ⟩—NO₂ with COOH | +220 |
| II. | " | —⟨ ⟩—COOH | " | " | " | +200 |
| III. | " | —⟨ ⟩—Cl with COOH | " | " | —O—⟨naphthyl⟩=O | NA |
| IV. | " | —⟨ ⟩—NO₂ with COOH | " | " | " | NA |
| V. | " | —⟨ ⟩—COOH | " | " | " | +200 |

TABLE I-continued

| RIND Compound | R⁶ | R² | R⁴ | R³ | FRAG | E₁ (mV.NHE) |
|---|---|---|---|---|---|---|
| VI. | —⟨benzene⟩—COOH | —⟨benzene⟩—CN | " | " | " | +220 |
| VII. | —CH₃ | —⟨benzene⟩—CN | " | " | —O—⟨naphthalene with SO₂NH—⟨benzene with 2 COOH⟩⟩—N=N—⟨benzene with SO₂CH₃ and NO₂⟩ | +220 |
| VIII. | " | —⟨benzene⟩—COOH | " | " | " | +200 |
| IX. | " | —⟨benzene⟩—COOH | " | " | —O—⟨naphthalene with NHSO₂—⟨benzene-SO₂NH₂⟩⟩—N=N—⟨benzene with SO₂CH₃ and NO₂⟩ | +200 |
| X. | " | —⟨benzene⟩ | R³ and R⁴ together form ⟨cyclopropane fused⟩ | | —O—⟨benzene with NO₂ and COOH⟩ | +222 |
| XI. | —⟨benzene⟩—COOH | —⟨benzene⟩ | " | " | —O—⟨acenaphthylenone⟩ | +222 |

RIND compound V is preferred in the practice of this invention.

Some water-compatible reducible compounds of this invention can be prepared by the general synthetic procedures described in U.S. Ser. No. 824,766, noted above. Others, e.g. RIND Compounds II–V, VII and IX of Table I, are prepared by novel procedures like those shown in Examples 1–3 below, involving oxazine ring opening using manganese dioxide and hydrolysis of the t-butylester group using trifluoroacetic acid.

Other water-compatible RIND compounds useful in the practice of this invention include those having the appropriate E₁ values, one or more water-compatibilizing moieties as described above, and the structure CAR—(R¹)ₙ wherein:

(1) CAR— is a substituted or unsubstituted nucleus of a 1,2-naphthoquinone, 1,2-, 1,4- or 9,10-anthraquinone, 4,4'-diphenoquinone, azuloquinone or 1,6-[10]-anulenoquinone wherein R¹ is attached to the nucleus one carbon atom distant or in the peri position from one of the oxo groups of the nucleus. The nucleus can be substituted with one or more electron withdrawing groups as described above for R² or have one or more strained fused rings as described above for R³ and R⁴. R¹ is

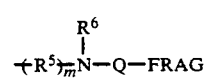

as defined above, and n is an integer of 1 or 2.

(2) CAR— is 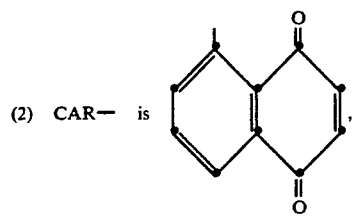,

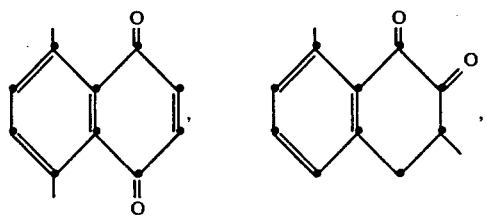

-continued

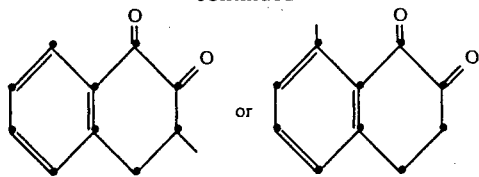

any of which can be substituted with one or more electron withdrawing groups as described above for $R^2$, $R^3$ and $R^4$. $R^1$ is

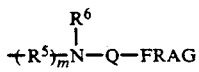

as defined above, and n is 1 or 2.

(3) CAR— is a substituted or unsubstituted nitrobenzenoid nucleus of the structure

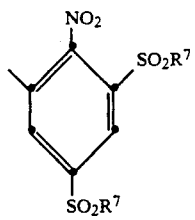

wherein $R^7$ is substituted or unsubstituted alkyl of 1 to 12 carbon atoms (e.g. methyl, ethyl, methoxymethyl, isopropyl, dodecyl, etc.), and $R^1$ is

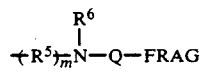

as defined above and n is 1. These compounds are similar to some described in U.S. Pat. No. 4,139,379.

All of these reducible compounds can be prepared using techniques and starting materials known in the art or readily apparent to a skilled synthetic chemist.

The water-compatible reducible compounds described herein can be prepared as an aqueous composition comprising a suitable buffer, and optionally a water-miscible solvent.

A composition can be prepared in the following general manner with the particular details of such a preparation illustrated in Example 4 below. The reducible compound is dissolved in the buffer at a concentration which depends upon its molecular weight, but generally at from about 1 to about 100, and preferably from about 5 to about 80, mg per ml of buffer. Alternatively, the reducible compound can be dissolved in the water-miscible solvent and then mixed with a suitable buffer.

The buffer generally maintains the assay at physiological pH (9 or less). The concentration of buffer in the aqueous composition can vary widely, but is generally from about 0.01 to about 0.1 molar. Representative buffers include phosphates, borates and others reported by Good et al in *Biochemistry*, 5, 467 (1966), and *Anal. Biochem.*, 104, 300 (1980).

The water-compatible reducible compounds described herein are useful in compositions for analytical determination (i.e. qualitative or quantitative detection) of aqueous and nonaqueous liquids, e.g. biological fluids, manufacturing processes, wastewater, food stuffs, etc. Determinations can be made of various analytes via a single reaction or sequence of reactions which bring about reduction of the compound and release of the detectable species. The analytes include living cells (e.g. bacteria, white blood cells, yeast, fungi, etc.), enzymes (e.g. oxidoreductases such as lactate dehydrogenase, pyruvate dehydrogenase, glucose-6-phosphate dehydrogenase, etc., oxidases such as glucose oxidase, lactate oxidase, α-glycerophosphate oxidase, etc., transferases such as alanine aminotransferase, aspartate aminotransferase, etc., hydrolases such as lipase, carboxyesterase, etc. and other NADH-based, FADH-based or oxidase-based assays), biological or chemical reductants other than living cells which will reduce the reducible compound (e.g. ascorbates, cysteine, glutathione, thioredoxin, etc.), metabolizable substances (e.g. glucose, lactic acid, triglycerides, cholesterol, etc.), immunoreactants (e.g. antigens, antibodies, haptens, etc.).

The compositions can be used to monitor enzyme redox reactions as well as flavin adenine dinucleotide (FAD-FADH)-based and nicotinamide adenine dinucleotide (NAD-NADH)-based and (NADP-NADPH)-based reactions. In such instances, the reducible compound can be used to provide a detectable species in place of NADH, FADH or NADPH.

The present invention is particularly useful in detecting or quantifying living cells in biological samples. Although any biological sample suspected of having living cells therein (e.g. food, tissue, ground water, cooling water, pharmaceutical products, sewage, etc.) can be analyzed for bacteria, yeast, fungi, etc. by this invention, the invention is particularly useful for bacterial detection in aqueous liquids, such as human and animal fluids (e.g. urine, cerebral spinal fluid, blood and the like as well as stool secretions) and suspensions of human or animal tissue. The practice of this invention is particularly important for detection of urinary tract infections in urine (diluted or undiluted).

When determining living cells using the reducible compounds, it is preferable for rapid dye release in such determinations that the living cells interact with an electron transfer agent (herein ETA). The presence of an ETA may also provide more efficient dye release for analytical determinations of nonliving analytes. The ETA is a mobile compound which acts as an intermediary between the substance being determined (e.g. living cell) and the reducible compound. Some ETAs may work better than others in determining a given organism (see e.g. Example 11 below).

In general, the ETA compounds useful in the practice of this invention have an $E_{\frac{1}{2}}$ in the range of from about $-320$ to about $+400$ mV as measured in aqueous buffer (pH 7) versus the normal hydrogen electrode using a differential pulse polarographic technique with a PAR Potentiostat (Princeton Applied Research, Princeton, N.J.). In general, the potential of the ETA should be more positive than the potential of the substance to be determined (i.e. analyte) and less positive than the potential of the reducible compound. That is, the ETA should be more easily reduced than the analyte and less easily reduced than the reducible compound. They are generally present at a concentration that is dependant upon the concentration of the analyte, and preferably at a concentration of from about $1 \times 10^{-7}$ molar to about $1 \times 10^{-3}$ molar.

ETA compounds useful in the practice of this invention include phenazine methosulfate, phenazine ethosulfate and similar compounds known to one skilled in the art. Combinations of different ETA compounds can be used if desired.

Preferred ETA compounds useful in the practice of this invention which provide further advantages of low background are those which are the subject of copending and commonly assigned U.S. Ser. No. 699,374 filed by Mura et al Feb. 7, 1985. In general, those compounds are substituted benzo- and naphthoquinones. Examples of this class of quinones include 2,3-dimethyl-5-hydroxymethyl-1,4-benzoquinone, 2,5-dimethoxy-1,4-benzoquinone, 2,3,5-trimethyl-1,4-benzoquinone, tetramethyl-1,4-benzoquinone, 2,3-dimethoxy-5-methyl-1,4-benzoquinone, 2-hydroxymethyl-1,4-naphthoquinone and 2-(2-hydroxyethyl)-1,4-naphthoquinone.

The detection of living cells, and particularly of microorganisms, is often carried out in the presence of a nutrient for those cells although its presence is not essential. Any nutrient media can be used which contains useful carbon, and optionally nitrogen, sources. Suitable nutrient media having proper components and pH are well known in the art. Particularly useful nutrients are glucose or tryptose alone or in combination.

The present invention is adaptable to either solution or dry assays. In a solution assay, a solution containing a reducible compound, and preferably an ETA, is prepared and contacted and mixed with a liquid test sample suspected of containing the living cells or analyte to be determined. The ETA can also be mixed with the test sample prior to mixing with the reducible compound. Generally the reducible compound is mixed with the test sample in a suitable container (e.g. test tube, petri dish beaker, cuvette, etc.). The resulting solution is gently mixed and incubated for a relatively short time (i.e. up to about 30 minutes) at a temperature up to about 40° C., and generally from about 20° to about 40° C. The test sample is then evaluated by measuring the detectable species, for example, at a wavelength in the spectral absorption band of a chromagen species, or at a wavelength in the emission band of a fluorogen species which band is different than the band the reducible compound had prior to species release. Such an evaluation can be done with suitable detection equipment.

A pretreatment step to remove interferents or to concentrate cells can also be carried out before the assay, if desired.

A solution assay can also be carried out by contacting a porous, absorbent material, e.g. paper strip, containing the test sample with a solution of the reducible compound. The analyte in the test sample can migrate from the porous material into the solution and initiate the analytical reactions needed for determination. In solution assays, the amount of water-compatible reducible compound present is at least about 0.001, and preferably from about 0.01 to about 1.0, millimolar. Other reagents can be present in amounts readily determined by one skilled in the art.

Alternatively, the method of this invention can be practiced in a dry assay with a dry analytical element. Such an element can be a absorbent carrier material, i.e. a thin sheet or strip of self-supporting absorbent or bibulous material, such as filter paper or strips, which contains the reducible compound or a dried residue of the dispersion comprising same. Such elements are known in the art as test strips, diagnostic elements, dip sticks, diagnostic agents and the like.

When employed in dry analytical elements, the reducible compounds described herein can be incorporated into a suitable absorbent carrier material by imbibition or impregnation, or can be coated on a suitable absorbent carrier material. Alternatively, they can be added to the element during an assay. Useful carrier materials are insoluble and maintain their structural integrity when exposed to water or physiological fluids such as urine or serum. Useful carrier materials can be prepared from paper, porous particulate structures, cellulose, porous polymeric films, glass fiber, woven and nonwoven fabrics (synthetic and nonsynthetic) and the like. Useful materials and procedures for making such elements are well known in the art as exemplified by U.S. Pat. Nos. 3,092,465 (issued Jun. 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued Jun. 2, 1981 to Kondo et al).

A dry assay can be practiced to particular advantage with an analytical element comprising a support having thereon at least one porous spreading zone as the absorbent carrier material. The reducible compound can be in the spreading zone or in a different zone (e.g. reagent zone, registration zone, hydrophilic zone, etc.). The spreading zone can be prepared from any suitable fibrous or non-fibrous material or mixtures of either or both.

The spreading zone can be prepared using fibrous materials, either mixed with a suitable binder material or woven into a fabric, as described in U.S. Pat. No. 4,292,272 (issued Sep. 29, 1981 to Kitajima et al), from polymeric compositions (e.g. blush polymers) or particulate materials, with or without binding adhesives, as described in U.S. Pat. Nos. 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese Patent Publication 57(1982)-101760 (published Jun. 24, 1982). It is desirable that the spreading zones be isotropically porous, meaning that the porosity is the same in each direction in the zone as created by interconnected spaces or pores between particles, fibers, polymeric strands, etc.

The dry analytical element of this invention can be a single self-supporting porous spreading zone containing a reducible compound and any other desired reagents for a particular use, but preferably such zone is carried on a suitable support. Such a support can be any suitable dimensionally stable, and preferably, nonporous and transparent (i.e. radiation transmissive) film or sheet material which transmits electromagnetic radiation of a wavelength between about 200 and about 900 nm. A support of choice for a particular element should be compatible with the intended mode of detection (reflection, fluorescence or transmission spectroscopy) and inert to chemical reagents and liquid samples used in the assay. Useful support materials include polystyrene, polyesters [e.g. poly(ethylene terephthalate)], polycarbonates, cellulose esters (e.g. cellulose acetate), etc.

The elements can have more than one zone, e.g. a reagent zone, a registration zone, subbing zone, etc. The zones are generally in fluid contact with each other, meaning that fluids, reagents and reaction products can pass between superposed regions of adjacent zones. Preferably, the zones are separately coated superposed layers, although two or more zones can be in a single coated layer. Besides the patents noted above, suitable element formats and components are described also, for example, in U.S. Pat. Nos. 4,042,335 (issued Aug. 16, 1977 to Clément) and 4,144,306 (noted above) and Reissue 30,267 (reissued May 6, 1980 to Bruschi).

In the elements of this invention, the amount of the water-compatible reducible compound can be varied widely, but it is generally present in a coverage of at least about 0.01, and preferably from about 0.05 to about 0.2, g/m². Optional, but preferred reagents (e.g. ETA, nutrient, buffer, etc.) are generally present in the following coverages:

| | |
|---|---|
| ETA: | generally at least about 0.001, and preferably from about 0.01 to about 1, g/m², |
| nutrient: | generally at least about 0.05, and preferably from about 0.1 to about 2, g/m² (used only in living cell detection), and |
| buffer (pH ≦ 9): | generally at least about 0.1, and preferably from about 0.5 to about 2, g/m². |

One or more of the zones can contain a variety of other desirable, but optional, components, including activators, binders (generally hydrophilic), antioxidants, etc. as is known in the art, as well as any reagents needed for assay of a particular analyte.

In one embodiment of this invention, an element for detection of organisms (e.g. yeast, fungi, bacteria, etc.) in an aqueous liquid comprises an electron transfer agent and a reducible compound, both of which are described above. It is desirable that these elements also contain a nutrient for the living cells and a buffer which maintains physiological pH during the assay (e.g. when contacted with a 1-200 µl sample of test liquid). Such an element can be used to detect bacteria, for example, in a urine sample (e.g. one pretreated to eliminate interferents or to concentrate cells) by physically contacting the sample and element in a suitable manner, and detecting the detectable species released from the reducible compound as a result of the presence of the bacteria at the appropriate wavelength.

In another embodiment of this invention, an element is used for the determination of a nonliving biological or chemical analyte in an aqueous liquid. If the analyte is not capable of directly reducing the reducible compound described herein to release a detectable species, the assay also includes the use of an interactive composition comprising one or more reagents which interact with the analyte to produce a product which will reduce the reducible compound. This interactive composition can be incorporated into the element or added at the time of the assay. Examples of such analytes are described above. The amount of detectable species detected can be correlated to the amount of analyte present in the liquid sample.

The element of this invention is also useful for determining other reductants such as ascorbate (ascorbic acid and equivalent alkali metal salts), cysteine, glutathione, thioredoxin and the like.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, an analyte or living cell determination is made by taking the element from a supply roll, chip packet or other source and contacting it with a sample (e.g. 1-200 µl) of the liquid to be tested so that the sample mixes with the reagents in the element. Such contact can be accomplished in any suitable manner, e.g. dipping or immersing the element into the sample or, preferably, by spotting the element by hand or machine with one or more drops of the sample with a suitable dispensing means.

After sample application, the element is exposed to any conditioning, such as incubation, heating or the like, that may be desirable to quicken or otherwise facilitate obtaining any test result.

Detection of an analyte or living cell is achieved when the water-compatible reducible compound is reduced releasing a species which can be detected in a suitable manner. Preferably, as noted above, the detectable species is a colorimetric dye or fluorescent dye which can be detected with standard colorimetric or fluorometric apparatus and detection procedures. If the detectable species is other than a chromogen or fluorogen, for example, a chemiluminescent or phosphorescent moiety, suitable chemiluminescence or phosphorescence detecting means can be employed. Spectral determinations can be made at the maximum wavelength of the detectable species or at wavelengths other than the maximum wavelength.

Reagents used in the following examples were obtained as follows: N-2-hydroxyethylpiperizine-N'-2-ethanesulfonic acid (HEPES) buffer and phenazine methosulfate from Sigma Chemical Co. (St. Louis, Mo., U.S.A.), brain heart infusion broth (BHI) and Sabaroud's dextrose (SAB) broth from Difco Labs (Detroit, Mich., U.S.A.), TRITON X-100 surfactant from Rohm & Haas (Philadelphia, Pa., U.S.A.), and the bacterial microorganisms from the American Type Culture Collection (ATCC) in Rockville, Md., U.S.A.. All other reagents were either obtained from Eastman Kodak Company (Rochester, N.Y., U.S.A.) or prepared using known starting materials and procedures.

*Escherichia coli* (ATCC 25922) and *Staphylococcus aureus* (ATCC 25923) cells were individually grown overnight in BHI medium at 37° C. without shaking and transferred daily. Forty ml of the cells were harvested by centrifugation and resuspended in 10 ml of a 0.05 molar HEPES buffer (pH 7.8). The absorbance measured at 620 nm was adjusted to 0.5 and 1.0, respectively. An absorbance of 0.833 (620 nm) was found to be equivalent to about $5 \times 10^8$ cells/ml. *Candida albicans* (ATCC 14053) cells were grown in SAB broth overnight at 25° C. with agitation, harvested by centrifugation, washed and resuspended in HEPES buffer. The cell suspension was adjusted to an optical density of about 1.0.

In the preparation of the illustrated reducible compounds, the identity and purity of the intermediates were determined by infrared (IR) spectra as measured in a commercially available Perkin-Elmer 137 spectrophotometer [sharp(s) or broad(b) bands yielding structural information are reported in reciprocal centimeters (cm$^{-1}$)], by nuclear magnetic resonance (NMR) spectra measured in a standard Perkin-Elmer NMR spectrophotometer [chemical shifts reported in δ values in ppm to tetramethylsilane at broad(b), singlet(s), multiplet(m) or broad singlets(bs) peaks], or by field desorption mass spectral analysis (FDMS) measured in a Varian MAT 731 Spectrophotometer. The identity and purity of final products were determined by IR, NMR spectroscopy FDMS, and elemental analysis.

The following examples are presented to illustrate the practice of this invention. The identified RIND compounds are the reducible compounds included in Table I above.

EXAMPLE 1

Preparation of RIND Compound I

The Intermediates A'-F' for making RIND Compound I of Table I above were prepared according to the procedures of Steps 1-6 of Example 1 of U.S. Ser. No. 824,766, noted above, using p-cyanoaniline as a starting material instead of p-nitroaniline in Step 1.

The carbamoyl chloride from Step 6 was converted to Intermediate G' by the following procedure: carbamoyl chloride (15.8 g, 40 mmole) was added to a solution of t-butyl-5-hydroxy-2-nitrobenzoate (8 g, 33 mmole) and N,N-dimethylaminopyridine (catalytic amount) in pyridine (150 ml) and the resulting mixture was stirred for 18 hours under a nitrogen atmosphere in the dark. The reaction mixture was then poured into dilute hydrochloric acid/ice water (2 liters) and the precipitated yellow solid isolated by filtration, washed with water and air dried. Column chromatography (silica, 97:3, dichloromethane:ether) gave 19 g (96% yield) of Intermediate G' as a yellow foam. Analysis confirmed the structure: IR (KBr) cm$^{-1}$, 2250 (w, CN), 1725 (bs, —CO—), 1650 (s, quinone), NMR (CDCl$_3$) δ, 1.2–2.0 (m, bicyclic H's), 1.5 (s, t-butyl), 2.8–3.0 (d, NCH$_3$), 3.25–3.5 (bd, CH$_2$-N), 4.3–4.55 (bd, bridgehead), 7.15–8.0 (m, ArH's).

Intermediate G' was then converted to RIND Compound I by the following procedure. A solution of Intermediate G' (19 g, 31.8 mmole) and trifluoroacetic acid (75 ml) in dichloromethane (200 ml) was stirred under a nitrogen atmosphere in a dark area for 2.25 hours. The reaction mixture was poured into ice water and the layers were separated. The organic layer was washed with cold water, dried (sodium sulfate) and the solvent removed to give a yellow foam. This material was filtered through silica using 95:5 dichloromethane:ether to give 10 g (58% yield) of RIND Compound I. IR (KBr) cm$^{-1}$, 2250 (w, CN), 1730 (bs, —CO—), 1650 (s, quinone). NMR (CDCl$_3$) δ 1.2–2.0 (m, bicyclic H's), 2.7–3.1 (d, NCH$_3$), 3.35–3.36 (m, bridgehead H's), 4.3–4.55 (d, —CH$_2$—N), 6.9–8.0 (m, ArH's). Elemental analysis also confirmed the structure.

EXAMPLE 2

Preparation of RIND Compound V

Intermediates A'-D' for the preparation of RIND Compound V of Table I above were prepared according to the procedures of Steps 1-4 of Example 1 of U.S. Ser. No. 824,766, noted above, using 4-amino-t-butylbenzoate as a starting material instead of p-nitroaniline in Step 1.

Intermediate D' was converted to Intermediate E' by the following novel procedure: a suspension of Intermediate D' (20 g, 47.4 mmole) and manganese dioxide, activated (Aldrich Chemical Co., Milwaukee, Wis., U.S.A., 40 g, 474 mmole) in dicloromethane (1 liter) was stirred for 1 hour at 25° C. The mixture was filtered through a celite pad and the filtrate was concentrated under reduced pressure to give 19 g of the desired amine intermediate. NMR (CDCl$_3$), δ 1.1–1.9 (m, bicyclic ring H's), 1.6 (s, t-butyl), 1.85 (s, CH$_3$CN), 3.1–3.45 (m, bridgehead and CH$_2$N), 7.1 and 8.1 (AA'XX', J=9 cps, ArH's).

Intermediate E' was converted to Intermediate F' by the procedure of Step 6 of Example 1 of U.S. Ser. No. 824,766, noted above. Intermediate F' was converted to Intermediate G' by the procedure of Step G of Example 21 of U.S. Ser. No. 824,766.

Intermediate G' was converted to RIND Compound V using the following procedure carried out in the dark. A solution of Intermediate G' (9.1 g, 14.4 mmole) and trifluoroacetic acid (40 ml) in methylenedichloride (130 ml) was stirred under nitrogen for 2.5 hours. The solvent was removed under reduced pressure and the residue was dissolved in a minimal amount of acetone. The acetone solution was slowly added to a dilute solution of hydrochloric acid in ice water (400 ml) and the resulting semisolid was collected by filtration, washed with water and air dried. The material was recrystallized from ethyl acetate to give 6.3 g of RIND Compound V as a yellow solid. IR (KBr) cm$^{-1}$, 1730 (bs, —CO—), 1650 (s, quinone —CO—). NMR (CDCl$_3$) δ 1.1–2.0 (m, bicyclic H's), 2.9 (d, 12 ppm, CH$_3$N), 3.35 (d, 9 ppm, bridgehead H's), 4.5 (d, 16 ppm, —CH$_2$N), 6.45–8.6 (m, phenalenone and Ar —COOH). Elemental analysis: Calculated for C$_{35}$H$_{27}$NO$_7$: C, 73.3, H, 4.7, N, 2.4. Found: C, 73.2, H, 5.1, N, 2.2.

EXAMPLE 3

Preparation of RIND Compound VI

The quinone nucleus was prepared by a standard oxidation of the corresponding hydroquinone, which had been prepared according to the procedure described in Steps 1-3 of Example 1 in U.S. Ser. No. 824,766 of Belly et al., reference above, using p-cyanoaniline instead of p-nitroaniline.

This quinone (5.2 g, 18 mmole) was added to a mixture of hydrobromic acid (30% in acetic acid, 48 ml), 37% formalin (18 ml) and acetic acid (140 ml), and the resulting solution was heated at 55° C. for 18 hours. After cooling, the reaction mixture was poured into ice water (500 ml), and the precipitated yellow solid was collected and recrystallized from ethanol to give 2.4 g of the bromomethyl intermediate having a m.p. of 201°–202° C. An NMR spectrum confirmed the structure.

A mixture of the bromomethyl intermediate (9.2 g, 24 mmole), p-amino-t-butylbenzoate (9.25 g, 48 mmole) and silver(I)carbonate (6.6 g, 24 mmole) in N,N-dimethylformamide (360 ml) was stirred under a nitrogen atmosphere in a dark area for 36 hours. The resulting mixture was poured into dilute hydrochloric acid/ice water (1500 ml) and the precipitated brown solid was collected by filtration, washed with water and dried under reduced pressure in a desiccator. Chromatography (silica, 70:30 ligroine:ethyl acetate) afforded the desired amine intermediate, yield of 7 g. Mass spectral analyses, nuclear magnetic resonance and infrared spectroscopy confirmed the structure.

The amine intermediate was converted to the corresponding carbamoyl chloride by the procedure described in Step 6, Example 1 of the Belly et al application noted above.

A mixture of the carbamoyl chloride (7 g, 12.6 mmole), 6-hydroxyphenalenone (2.05 g, 10.4 mmole), prepared by the procedure described in U.S. Ser. No. 824,757 of Babb et al., filed Jan. 31, 1986 and entitled BIOLOGICAL AND ANALYTICAL USES OF PHENALENONE AND BENZPHENALENONE COMPOUNDS, now U.S. Pat. No. 4,803,161 and N,N-dimethylaminopyridine (catalytic amount) in pyridine (75 ml) was stirred under nitrogen in a dark area for 18 hours. The mixture was poured into dilute hydrochloric acid/ice water and the precipitated solid was collected by filtration, washed with water and dried in air in a dark area. Chromatography (silica, 98:2, dichloromethane:acetone) gave 5 g of the desired intermediate. An analytical sample was obtained by recrystallization from ether to give a pale yellow solid. NMR (CDCl$_3$)δ, 1.2-2.0 (m, —CH$_2$CH$_2$— of bicyclic ring), 1.6 (s,t-butyl), 3.21-3.59 (m, bridgehead H's), 4.9 (s, —CH$_2$N—), 6.6-6.75 (d, dye H's), 7.1-8.2 (m, dye and aryl H's), 8.6-8.7 (d, dye H's). IR (KBr) cm$^{-1}$, 2240 (s, CN), 1720 (b, C=O), 1640 (s, quinone).

A solution of the t-butylcarboxyphenyl intermediate (2 g, 2.8 mmole) and trifluoroacetic acid (10 ml) in dichloromethane (25 ml) was stirred under a nitrogen atmosphere in a dark area for 2 hours. The reaction solution was concentrated in a dark area to remove the solvent and the residue was dissolved in tetrahydrofuran and the solution was poured into dilute hydrochloric acid/ice water. The precipitated solid was collected by filtration, washed with water and dried in a dark area. Column chromatography (silica, 89.5 dichloromethane, 10 acetone, 0.5 acetic acid) afforded 1.4 g of RIND Compound VI of Table I above as a yellow solid. IR (KBr, cm$^{-1}$), 2250 (w, CN), 1720 (bs, C=O), 1645 (s, quinone). NMR (CDCl$_3$)δ, 1.15-2.0 (m, bicyclic H's), 3.2-3.5 (d, bridgehead H's), 4.95 (s, CH$_2$N), 6.6-8.7 (m, ArH's). Elemental analysis also confirmed the structure.

EXAMPLE 4

Preparation of Aqueous Composition

Compositions of this invention were prepared as follows: the appropriate RIND compound was dissolved in 250 ml of N,N-dimethylformamide (DMF), which had been acidified by the addition of 0.1% concentrated sulfuric acid, and the resulting solution was added to 25 ml of 0.05 molar potassium phosphate buffer or 0.05 molar HEPES buffer (pH 7.8).

EXAMPLES 5 and 6

Assay for E. coli: Comparison of Water-Compatible RIND Compounds With and Without Surfactant This example uses two water-compatible RIND Compounds of this invention (I and X of Table I above) in a comparison of an assay of the present invention using a composition without surfactant to an assay of Belly et al U.S. Ser. No. 824,766 using a composition including a surfactant.

E. coli cells were grown overnight in BHI medium without shaking at 37° C. Forty milliliters of cells were harvested by centrfugation. The resulting pellet was resuspended in 25 ml potassium phosphate buffer (pH 7.5, μ=0.05) and the resulting suspension was centrifuged. The pellet was washed and resuspended in 25 ml of buffer, and an aliquot of the suspension was diluted with the same buffer to obtain an absorbance of 0.1 at 620 nm.

A. Compositions of the present invention were prepared from the following solutions: phenazine methosulfate (PMS) or 2-hydroxymethyl-5,6-dimethyl-1,4-benzoquinone (HDMBQ) (9.8×10$^{-3}$ molar in methanol), RIND Compounds I or X (1.7×10$^{-2}$ molar in N,N-dimethylformamide, DMF), and glucose solution (10% in water).

A 1 cm pathlength cuvette (4 ml capacity) was filled with 0.1 ml cell suspension, (final concentration 6×10$^{-7}$ cells/ml), 3.0 ml phosphate buffer, 50 μl glucose solution (final concentration 8.8×10$^{-2}$ molar), and 25 μl of either PMS or HDMBQ (final concentration 7.7×10$^{-5}$ molar). The cuvette was sealed to prevent evaporation and thermally equilibrated at 37° C. The reaction was initiated by the addition of 14 ml of RIND Compound I or X (final concentration 7.6×10$^{-5}$ molar). Control solutions were prepared without any cells.

B. Compositions of the prior art using TRITON X-100 surfactant were prepared from the following solutions: (1) PMS or HDMBQ (9.8×10$^{-3}$ molar in methanol), (2) RIND Compound I or X (7.1×10$^{-2}$ molar in DMF), (3) 50 μl of solution 2 plus 100 μl TRITON X-100 surfactant plus 5 ml phosphate buffer, (4) glucose solution (10% in water), and (5) 6×10$^9$ cells/ml in phosphate buffer.

A 1 cm pathlength cuvette was filled with 188 ml of solution 3, final RIND concentration 7.6×10$^{-5}$ molar, 6 μl of solution 4, final glucose concentration 8.8×10$^{-3}$ molar, and 12.5 μl of solution 5, final cell concentration 6×10$^{-7}$ cells/ml. The cuvette was covered and thermally equilibrated at 37° C. The reaction was then initiated by the addition of 3 μl of solution 1, final ETA concentration 7.7×10$^{-5}$ molar. Control solutions were prepared without any cells.

Reactions ere followed by monitoring the appearance of dye at 402 nm. The results, shown in Table II below, are averages of 3 or 4 determinations and indicate the increased cell response from compositions of this invention.

TABLE II

| RIND Compound | ETA | % Dye Released After 10 Minutes | |
|---|---|---|---|
| | | With E. Coli.: | Without E. Coli.: |
| I | PMS | 60 | 1.3 |
| I (Control) | " | 49 | 0.7 |
| I | HDMBQ | 53 | 0.8 |
| I (Control) | " | 31 | 0.1 |
| X | PMS | 83 | 1.2 |
| X (Control) | " | 56 | 1.1 |
| X | HDMBQ | 86 | 1.4 |
| X (Control) | " | 65 | 0.7 |

EXAMPLE 7

Comparative Assays Using Water-Compatible RIND and Water-Incompatible RIND Compounds Assays were run in a Milliliter HA 96 Well Filtration Plate (Millipore Corp., Bedford, Mass., U.S.A.). Fluorescence was measured using a Dynatech Microfluor Reader (Dynatech Laboratories, Alexandria, Va., U.S.A.) modified to read at excitation 510 nm and emission 620 nm.

A Control composition was prepared as follows: 250 μl of RIND solution (16 mg of Control RIND compound/ml acidified DMF), 500 μl TRITON X-100 surfactant solution, 25 ml HEPES buffer (pH 7.8), 500 μl trimethyl-1,4-benzoquinone (TMBQ) (1.5 mg/ml methanol), and 500 μl glucose solution (10% solution in water). The Control RIND compound was like Compound V of Table I above except that it has a cyano group in place of the carboxy group.

A composition of this invention was prepared as follows: 250 μl of RIND V (16 mg/ml of acidified DMF), 25 μl HEPES buffer, 500 μl TMBQ (1.5 mg/ml methanol) and 500 ml glucose solution (10% in water).

The assays were carried out in duplicate by adding 150 μl of *S.aureus* cell suspensions (final concentration $1\times10^{-7}$ cells/ml) to the wells, warming the plate to 37° C. and adding 150 μl of the control and test compositions. Blank solutions were prepared without any cells. Fluorescence was then measured at zero time and after 30 minutes incubation at 37° C. Data are shown in Table III below. These data indicate that the present invention provides increased release of dye in the absence of a surfactant.

TABLE III

| | Δ Relative Fluorescence, 30 minutes | |
|---|---|---|
| | Blank | *S. Aureus* |
| Control | 155 | 2787 |
| Test | 133 | >4000 |

EXAMPLE 8

Comparison of Cell Response with Water-Compatible RIND Compounds With and Without Surfactant This example illustrates the increased cell response in compositions of this invention using two water-compatible RIND compounds and four electron transfer agents.

RIND compounds used were VI and XI from Table I above. ETA's used were: ETA 1, tetramethyl-1,4-benzoquinone, ETA 2, 2,3,5-trimethyl-1,4-benzoquinone, ETA 3, 2,3-dimethoxy-5-methyl-1,4-benzoquinone, ETA 4, 2-hydroxymethyl-1,4-naphthoquinone.

Solutions were prepared from each watercompatible RIND compound and each ETA in microtitration plates. Control solutions (with TRITON X-100 surfactant) contained the following: 9.3 ml HEPES buffer (pH 7.8), 0.1 μl RIND compound (final concentration $7.6\times10^{-5}$ molar in acidified DMF), 0.2 μl TRITON X-100 surfactant, 0.2 μl 10% glucose solution, 0.2 μl ETA (final concentration $3.85\times10^{-5}$ molar in methanol) and 0.15 μl *E.coli* cells (final concentration $10^7$ cells/ml HEPES buffer). Test solutions were prepared from the same components, except no TRITON X-100 surfactant was present. Blank solutions were prepared containing all components except cells for background measurements. Fluorescence was then measured at zero time and after 30 minutes incubation at 37° C. Data are shown in Table IV below. These data indicate that more dye is released in the absence of surfactant in all tests.

a composition of U.S. Ser. No. 824,766, identified above.

A composition of this invention was prepared as described above in Example 7. Control A composition was prepared similarly to the Control composition of Example 7 whereas Control B was the same as Control A except that the RIND compound used was a water-compatible compound of this invention (RIND V). Both Controls A and B contained a surfactant.

Blood samples (8.5 ml) were collected in standard blood collection tubes containing 1.5 ml of acid citrate dextrose. A 6% dextran solution was added to each at a volume of from 1.5 to 2 ml per tube, and the tube contents were mixed by inversion and allowed to settle for 1.5 hours. The plasma layer from each tube was transferred to sterile 15 ml centrifuge tubes and 0.5 molar potassium phosphate buffer (pH 7.5) containing 8.9 g/l NaCl was added. The tubes and their contents were then centrifuged at 1000 rpm for 10 minutes and the supernatant decanted. The resulting cell pellet was resuspended in 10 ml lysing solution (8.3 g ammonium chloride, 1 g sodium carbonate and 0.03 g sodium ethylenediaminetetraacetic acid per liter), and then the tubes were allowed to stand for 5 minutes to allow the solution to clear. The tube contents were again centrifuged at 1000 rpm for 10 minutes, and the supernatant decanted. Again, the resulting pellet was resuspended in phosphate buffered saline, centrifuged, the supernatant decanted and the pellet resuspended in 0.5 ml phosphate buffered saline.

White blood cells were counted after preparation by standard procedures using a commercially available Coulter Counter instrument equipped with a 30 ml aperture. The counts were corrected for coincidence. The cells were refrigerated overnight prior to evaluation and then diluted 25 fold in phosphate buffered saline prior to use.

To microliter plate wells were added diluted white blood cell suspension (150 μl at $2.1\times10^5$ cells/ml), a RIND compound composition (150 μl), trimethylbenzoquinone ETA (25 μl of 1.5 mg/ml methanolic solution) and glucose (25 μl of 10% w/v). The plates were incubated at 37° C. and the dye released was evaluated by measuring the fluorescence (emission, 620 nm, excitation, 540 nm) using a commercially available fluorometer equipped with a Xenon arc lamp source. Three replicates of each test were made.

The results of the assays, shown in Table V below, indicate that white blood cells can only be detected using a water-compatible RIND compound in a composition lacking a surfactant.

TABLE IV

| | Δ Relative Fluorescence (minus background), 30 Minutes | | | | | | | | | | | | | | |
|---|---|---|---|---|---|---|---|---|---|---|---|---|---|---|---|
| | ETA | | | | | | | | | | | | | | |
| | 1 | | 2 | | 3 | | 4 | | | | | | | | |
| | RIND | | | | | | | | | | | | | | |
| | VI | | XI | | VI | | XI | | VI | | XI | | VI | | IX |
| Surfactant | − | + | − | + | − | + | − | + | − | + | − | + | − | + | − | + |
| Δ Rel. Fluor. | 724 | 407 | 731 | 580 | 1390 | 876 | 1303 | 1122 | 1281 | 317 | 1475 | 1005 | 1886 | 1389 | 1528 | 1328 |

EXAMPLE 9

Solution Assay of White Blood Cells

This example demonstrates the use of the present invention to determine white blood cells in a solution assay. It also compares a similar assay carried out with

TABLE V

| Composition | Δ Relative Fluorescence After 30 Minutes |
|---|---|
| Control A | −22 |
| Control B | −8 |

TABLE V-continued

| Composition | Δ Relative Fluorescence After 30 Minutes |
| --- | --- |
| Example 9 | 52 |

EXAMPLE 10

Determination of Bacteria and Yeast With a Dye Element Format

This example illustrates the determination of two species of bacteria, *E.coli* and *S.aureus* and a yeast *C.albicans* using a dry element containing RIND compound VI of Table I above.

Strips of Whatman 3 mm chromatography paper (VWR Scientific, Rochester, N. Y., U.S.A.) were immersed in the following solution: 7 ml methanol, 1 ml RIND solution (RIND VI, 0.028 molar in N,N-dimethylformamide containing 0.1% sulfuric acid), 1 ml ETA solution (2,3-dimethoxy-5-methyl-1,4-benzoquinone, 0.01 molar methanol) and 1 ml glucose solution (10% solution in water). The strips were then allowed to dry at 25° C. for 1 hour in a dark area.

A standard paper punch was used to cut discs [about ¼ inch (0.6 cm) in diameter] from the dried strips and the discs were placed in Corning Cell Wells TM. (Corning Glass Works, Corning, N.Y., U.S.A.).

Ten microliter samples of controls (containing only buffer) and test cell suspensions (*E.coli*, ~5×10$^8$ cells/ml, *S.aureus*, ~5×10$^8$ cells/ml, and *C.albicans*, ~5×10$^6$ cells/ml) were spotted onto the paper discs and fluorescence (excitation 540 nm, emission 620 nm) was measured at zero time and after 30 minutes of incubation at 37° C. using a Dynatech Microfluor Reader (Dynatech Labs, Alexandria, Va., U.S.A.). The results are shown in Table VI below as the change in relative fluorescence after 30 minutes. The average of two readings is listed. It is apparent that the present invention can be used to determine microorganisms with a dry element.

TABLE VI

| | Δ Relative Fluorescence, 30 Minutes, 37° C. |
| --- | --- |
| Control | 278 |
| E. coli | 2689 |
| S. aureus | 2570 |
| C. albicans | 2054 |

EXAMPLE 11

Assays for Various Organisms Using a Water-Compatible RIND Compound

This example illustrates the use of a reducible compound of this invention (RIND I of Table I above) for the determination of several organisms. All of the cells were grown as described above, without shaking, at 37° C., except *Micrococcus luteus* and *Bacillus subtilis* which were grown at 30° C., and *Pseudomonas aeruginosa* which was grown with shaking.

The assays were carried out as described in Examples 5 and 6 above. Two different ETAs, PMS and HDMBQ (both identified in Examples 5 and 6 above), were used. The resulting data are presented in Table VII below.

TABLE VII

| Organism | Final Cell concentration (cell/ml) | ETA | % Dye Released After 10 Minutes |
| --- | --- | --- | --- |
| *Bacillus subtilis* (ATCC 21777) | 1.7 × 10$^7$ | HDMBQ | 99 |
| | | PMS | 79 |
| *Micrococcus luteus* (ATCC 4698) | 1.5 × 10$^7$ | HDMBQ | 62 |
| | | PMS | 59 |
| *Proteus vulgaris* (ATCC 13315) | 9.8 × 10$^7$ | HDMBQ | 68 |
| | | PMS | 67 |
| *Pseudomonas aeruginosa* (ATCC 27853) | 3.5 × 10$^7$ | HDMBQ | 68 |
| | | PMS | 3 |
| *Serratia marcescens* (ATCC 8100) | 2.2 × 10$^8$ | HDMBQ | 12 |
| | | PMS | 21 |
| *Staphyloccus aureus* (ATCC 25923) | 7.6 × 10$^7$ | HDMBQ | 61 |
| | | PMS | 50 |
| *Streptococcus facaelis* (ATCC 33186) | 1 × 10$^8$ | HDMBQ | 41 |
| | | PMS | 20 |
| *Salmonella typhimurium* (ATCC 14028) | 1.4 × 10$^8$ | HDMBQ | 41 |
| | | PMS | 54 |
| *Klebsiella pneumoniae* (ATCC 13883) | 9.8 × 10$^7$ | HDMBQ | 37 |
| | | PMS | 59 |

The present invention has been described in detail with particular reference to preferred embodiments thereof, but it will be understood that variations and modifications can be effected within the spirit and scope of the invention.

We claim:

1. A method for providing a chemically or biologically useful moiety comprising, at a pH of 9 or less, reducing a water-compatible reducible compound of the structure CAR—(—R$^1$)$_n$ wherein CAR— is a substituted or unsubstituted aromatic or quinone nucleus, R$^1$ is a moiety which comprises a shiftable detectable species, and n is 1 or 2, provided said reducible compound is constructed such that it is capable of being reduced at said pH to release said shiftable detectable species, and said reducible compound comprises at least one water-compatibilizing moiety which has a hydrophobic parameter less than about −2.0 and which is selected from the group consisting of carboxy, sulfo, ammonium, sulfonamido, hydroxy, iodoxy and glucosyl, and further provided that when R$^1$ is replaced with H, CAR— (—H)$_n$ is constructed such that it has an E$_{½}$ of at least about +100 mV when measured in water.

2. The method of claim 1 wherein CAR— is

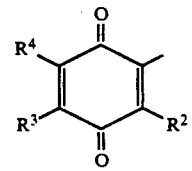

R$^1$ is

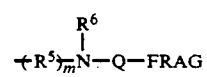

R$^2$ and R$^4$ are independently hydrogen, alkyl, aryl or an electron withdrawing group, R$^3$ is R$^1$, hydrogen, alkyl, aryl or an electron withdrawing group, provided at least one of R$^2$, R$^3$ and $R^4$ is an electron withdrawing group, or $R^3$ and $R^4$, taken together, represent the atoms necessary to complete a strained fused carbocyclic ring, $R^5$ is alkylene of 1 or 2 carbon atoms, $R^6$ is alkyl, cycloalkyl or aryl, FRAG is a species which provides a chemically or biologically useful moiety when released from said reducible compound, Q is carbonyl or thiocarbonyl, and m is 0 or 1, provided that when $R^1$ is replaced with H, CAR—H has an $E_{\frac{1}{2}}$ of at least about +100 mV when measured in water, and further provided that at least one of $R^1$, $R^2$, $R^3$ and $R^4$ contains at least one of said water-compatibilizing moieties.

3. The method of claim 2 wherein m is 1, at least two of $R^2$, $R^3$ and $R^4$ are independently electron transfer withdrawing groups, or $R^3$ and $R^4$, taken together, represent the atoms necessary to complete a strained fused 5- to 8-membered carbocyclic ring.

4. The method of claim 3 wherein $R^5$ is methylene, $R^6$ is methyl and Q is carbonyl.

5. The method of claim 2 wherein $R^2$, $R^6$ or FRAG comprises said water-compatibilizing moiety.

6. The method of claim 1 wherein said water-compatibilizing moiety is carboxy or sulfo.

7. The method of claim 6 wherein said water-compatibilizing moiety is carboxy.

8. The method of claim 1 wherein said chemically or biologically useful moiety is an electron transfer agent, enzyme, enzyme substrate, enzyme inhibitor or cofactor.

9. The method of claim 1 carried out in solution wherein said reducible compound is present at a concentration of at least about 0.001 mmolar.

10. The method of claim 1 carried out in a dry analytical element wherein said reducible compound is present within said element at a concentration of at least about 0.01 g/m².

* * * * *